| United States Patent [19]
Lipowski

[11] 3,936,494
[45] Feb. 3, 1976

[54] NAPHTHENOHYDROXAMIC ACID PREPARATION
[75] Inventor: Stanley A. Lipowski, Livingston, N.J.
[73] Assignee: Diamond Shamrock Corporation, Cleveland, Ohio
[22] Filed: Sept. 25, 1974
[21] Appl. No.: 509,283

[52] U.S. Cl....... 260/500.5 H; 204/45 R; 204/46 G; 204/47; 204/48; 204/49; 204/51; 204/52 R; 204/54 R; 204/55 R; 204/DIG. 2; 252/414; 260/429 J; 260/429.9; 260/430; 260/438.1; 260/439 R; 260/468 R; 423/8; 423/24; 423/57; 423/109; 423/138; 423/387
[51] Int. Cl.²...................................... C07C 119/00
[58] Field of Search............... 260/500.5 H; 423/387

[56] References Cited
UNITED STATES PATENTS

| 2,279,560 | 4/1942 | Dietrich.................... 260/500.5 H |
| 2,279,973 | 4/1942 | Dietrich.................... 260/500.5 H |
| 2,346,665 | 4/1944 | Cupery...................... 260/500.5 H |
| 2,397,508 | 4/1946 | Rouault et al............... 260/500.5 H |
| 3,282,986 | 11/1966 | Kaczka..................... 260/500.5 H |
| 3,345,344 | 10/1967 | Fetscher et al............. 260/500.5 H |
| 3,544,583 | 12/1970 | Burk et al.................. 260/500.5 H |
| 3,551,574 | 12/1970 | Frohberger et al......... 260/500.5 H |

FOREIGN PATENTS OR APPLICATIONS

| 852,176 | 10/1960 | United Kingdom.......... 260/500.5 H |
| 1,247,284 | 8/1967 | Germany........................ 423/387 |

*Primary Examiner*—Joseph E. Evans
*Attorney, Agent, or Firm*—Leslie G. Nunn

[57] ABSTRACT

Naphthenohydroxamic acid is prepared by reaction at 25°C to 30°C, equimolar quantities of
a. an ester of naphthenic acid,
b. hydroxylamine dissolved in an alcohol/water/alkali metal sulfate slurry wherein the water content of the slurry is insufficient to hydrolyze the ester during conversion to naphthenohydroxamic acid, and
c. an alkali metal hydroxide dissolved in alcohol.

Naphthenohydroxamic acid is useful as a chelating agent in hydrometallurgy to recover metal values from dilute solution.

9 Claims, No Drawings

NAPHTHENOHYDROXAMIC ACID PREPARATION

BACKGROUND OF THE INVENTION

1. Field of the Invention

This invention relates to naphthenohydroxamic acid, its preparation and use in hydrometallurgical processes to recover metal values and more particularly in liquid ion exchange processes.

2. Description of the Prior Art

U.S. Pat. No. 2,397,508 - G. F. Rouault and H. D. Rhodes, issued Apr. 2, 1946, describes preparation of naphthenohydroxamic acid from an ester of naphthenic acid by adding a dry hydroxylammonium salt such as the sulfate or chloride to the neutralized ester in alcohol and adding an aqueous sodium hydroxide solution to liberate the free hydroxylamine and convert the ester to the hydroxamic acid. The procedure is lengthy and yields are low.

U.S. Pat. No. 2,818,429 - Beretvas issued Dec. 31, 1957, describes an improved procedure for manufacture of naphthenohydroxamic acid from an ester of naphthenic acid by dissolving hydroxylammonium chloride in alcohol, adding the ester to the alcohol solution and neutralizing with an aqueous sodium hydroxide solution. The critical factors in this procedure are claimed to be: (1) the hydroxylammonium salt must be dissolved in alcohol; and (2) the amount of water in the reaction mixture must be not more on a weight basis than the amount of sodium hydroxide used.

This procedure is an improvement over the preparation described in U.S. Pat. No. 2,397,508 but it has two major disadvantages:

1. About one-third of the ester is decomposed because the saponification reaction is competing with the conversion of the ester to hydroxamic acid reaction. This is the result of addition of a water solution of metal hydroxide during the critical stage of the reaction when the ester is being converted to hydroxamic acid.

2. The most inexpensive source of hydroxylamine is hydroxylammonium sulfate, not hydroxylammonium chloride, which increases cost of the free base 2-3 times. The sulfate cannot be used in the process of U.S. Pat. No. 2,818,429 because it is completely insoluble in alcohol.

Hydrometallurgical processes for the treatment of ores and concentrates especially in the recovery of copper and nickel have been known to the mining industry for the last two decades. Some 15% of the copper produced in the United States is now produced by hydrometallurgical techniques and production of nickel from laterites is becoming standard practice through the world. The most important hydrometallurgical commercial process for copper employs substituted 2-hydroxybenzophenoximes. See, e.g., U.S. Pat. No. 3,428,488 - Swanson issued Feb. 18, 1969. This process involves extraction of copper from dilute leach solutions by a countercurrent process using a water insoluble organic solvent solution of the chelating agent to form a metal complex. The so formed metal complex remains dissolved in the organic phase at a much higher concentration than originally present in the leach solution. Recovery of copper is accomplished by stripping the organic phase with a strong (10-30%) sulfuric acid solution.

The principal disadvantages of processes using substituted 2-hydroxybenzophenoneoximes are the relatively high cost of the chelating agent, its low chelating capacity and the very strong acid required for stripping. The strong acid causes gradual deterioration of the capacity of the chelating agent.

U.S. Pat. No. 3,367,959, Fetscher and Lipowski, issued Feb. 6, 1968, discloses the preparation and use of oil soluble chelators which are amidoximes and hydroxamic acids containing ester moieties. These materials are expensive to prepare and because of the presence of the ester linkage tend to decompose under acid conditions.

There is a need for further improvements in chelating agents as well as in hydrometallurgical processes where these agents are to be used. If naphthenohydroxamic acid is to be useful as a chelating agent in metal recovery processes, it is important to obtain a product having the maximum chelating capacity; e.g., complete conversion of the ester group to a hydroxamic acid group which contains the chelating oxime moiety, $-C=N-OH$.

SUMMARY OF THE INVENTION

An improved naphthenohydroxamic acid process involves reaction at about 25°C to about 30°C, about equimolar quantities of a. an ester of naphthenic acid
b. hydroxylamine dissolved in an alcohol/water/alkali metal sulfate slurry wherein the water content of the slurry is insufficient to hydrolyze the ester during conversion to naphthenohydroxamic acid, and
c. an alkali metal hydroxide dissolved in alcohol.

When naphthenohydroxamic acid is prepared by the improved process of this invention, its chelating power approximates the theoretical maximum indicating that the conversion of ester to hydroxamic acid is substantially 100%.

Use of naphthenohydroxamic acid as a chelating agent in the recovery of metal values from aqueous solutions also provides an improved hydrometallurgical process. In this process, a dilute aqueous solution containing metal values is contacted with a solution of naphthenohydroxamic acid dissolved in a water insoluble organic solvent such as a hydrocarbon solvent. Reaction between the metal ions in the aqueous solution and the naphthenohydroxamic acid dissolved in the organic solution is very rapid so a very short contact time between the metal ions and the naphthenohydroxamic acid is required to form a complex with the metal ions. The naphthenohydroxamic acid is soluble in water insoluble organic solvents so it can be used to preferentially extract metal ions from the aqueous phase.

Further, the naphthenohydroxamic acid - metal ion complex is soluble in the organic solvent phase and concentrates in the organic solvent during extraction of metal ions from the aqueous solution. When the concentration of the complex in the organic solvent reaches the desired level, it is separated from the aqueous solution which has been depleted of metal ions and is contacted with an aqueous stripping medium or other suitable means to recover the metal ions.

DESCRIPTION OF THE PREFERRED EMBODIMENTS

The formula for naphthenohydroxamic acids is

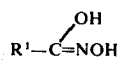

wherein $R^1$ is the hydrocarbon moiety of a naphthenic acid, a monocarboxylic acid of the naphthene (alicyclic) series of hydrocarbons. The general formula for naphthenic acids may be written as $R(CH_2)_nCOOH$ where R is a cyclic nucleus having one or more rings. These rings are usually 5-membered (cyclopentane) and may be alkylated.

The simplest naphthenic acid conforming to this formula when n=1 is cyclopentaneacetic acid

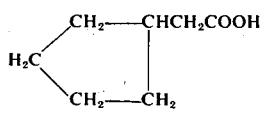

Naphthenic acids are natural components of crude petroleum and are not formed during refining. They are predominately monocarboxylic acids. Generally, the carboxyl group is not directly attached to the ring but through a methylene chain containing from one to five methylene groups.

The most important general types of naphthenic acids are $C_nH_{2n-2}O_2$, $C_nH_{2n-4}O_2$ and $C_nH_{2n-6}O_2$ (1, 2 and 3 rings). Naphthenic acids are well known in the art. They have been described in the literature in numerous publications and patents. Additional details on the chemical nature and properties of naphthenic acids may be found in Kirk-Othmer Encyclopedia of Chemical Technology, 2nd ed, vol. 13, pp. 727–734 and in Fieser & Fieser, Organic Chemistry, 2nd ed, pp. 91–92.

The process of the present invention employs an alkyl naphthenate which is obtained by esterification of one or more of the above naphthenic acids with an alcohol such as methanol, ethanol or propanol. If desired, the esterification may be carried out under pressure to obtain an ester having a purity of 96% or higher.

Further, the improved process employs hydroxylamine dissolved in an alkali metal sulfate-alcohol-water slurry. This slurry was discovered during study of naphthenohydroxamic processes and was developed because hydroxylammonium chloride previously used in such processes is an expensive chemical intermediate and is not commercially available in large quantities. The cheapest and most readily available hydroxylamine salt is hydroxylammonium sulfate. This sulfate is completely insoluble in an alcohol such as methanol, ethanol or propanol so any attempt to prepare a free hydroxylamine solution in alcohol by adding an alcoholic metal hydroxide solution such as alcoholic potassium hydroxide or sodium hydroxide solution to a hydroxylammonium sulfate slurry in alcohol fails. Further, an aqueous solution of hydroxylamine cannot be reacted with an alkyl naphthenate to produce the hydroxamic acid because hydrolysis of the alkyl naphthenate occurs at a faster rate in the aqueous medium than the reaction forming the hydroxamic acid potassium salt.

It was discovered that hydroxylamine can be dissolved in an alcohol/water/alkali metal sulfate slurry by
a. slurrying hydroxylammonium sulfate in water,
b. adding alcohol to the slurry,
c. cooling the slurry to about 0°C to about 5°C,
d. adding sufficient alkali metal hydroxide dissolved in water or alcohol to the slurry with agitation and cooling to a temperature below 5°C to adjust the final pH of the slurry to about 7 to about 8, and
e. adding sufficient alcohol to adjust the weight ratio of alcohol to water in the slurry to from about 2:1 to about 3:1.

The resulting hydroxylamine slurry is then reacted at about 25°C to about 35°C with about equimolar quantities of an ester of naphthenic acid and an alkali metal hydroxide dissolved in an alcohol to obtain the desired naphthenohydroxamic acid.

Useful hydroxylamine slurries may be prepared by
a. slurrying from about 64 to about 70 parts by weight of hydroxylammonium sulfate in from about 32 to about 40 parts by weight of water,
b. adding from about 48 to about 60 parts by weight of alcohol,
c. cooling at about 0°C to about 5°C,
d. adding sufficient sodium hydroxide dissolved in water or alcohol with agitation and cooling at a temperature below 5°C to obtain a slurry having a final pH from about 7 to about 8, and
e. adding sufficient alcohol to adjust the ratio of alcohol to water in the slurry to from about 2:1 to about 3:1.

In the above slurry preparations, the alkali metal dissolved in water or alcohol must be added at a slow rate with efficient cooling so that the temperature is maintained at 0°–10°C. The temperature at which the hydroxylammonium sulfate is neutralized and the final pH of the slurry are of extreme importance because the exothermic reaction will produce a sharp increase in temperature and too high a pH will cause rapid decomposition of the concentrated hydroxylamine solution.

After neutralization of the hydroxylammonium sulfate is complete, sufficient methanol is added to the slurry to adjust the weight ratio of alcohol to water in the slurry to about 2:1 to about 3:1 and then the ester of naphthenic acid, e.g., methyl naphthenate is added. Conversion of the ester to the hydroxamic acid is accomplished by a slow addition of alkali metal hydroxide dissolved in alcohol, e.g., a 25–30% potassium hydroxide solution in methanol using an amount of potassium hydroxide equivalent to the amount of ester present (one mole KOH to one mole ester). Temperature during this addition is maintained at 20°–25°C and rate of alkali metal hydroxide addition is regulated in such a way that any rapid increase in pH is avoided. When the reaction is carried out under these conditions, saponification of the ester is reduced to a minimum and substantially complete conversion of the ester to naphthenohydroxamic acid is obtained.

After all of the alkali metal hydroxide is added, the reaction mixture is stirred for an additional 3–4 hours, neutralized with a mineral or organic acid to a pH of about 7.0. Alcohol is removed from the reaction product by vacuum stripping and sufficient water is added to dissolve all of the salt present in the slurry. The mixture then separates into two phases (layers). The phases are separated and the desired product, naphthenohydroxamic acid (upper phase) is separated from the aqueous phase (lower phase), washed and dried by the addition of a solvent (kerosene, xylene, chlorinated solvent or the like) and azeotropic distillation. Filtration is not required. The amount of solvent remaining in the product will depend upon the activity desired. The activity may be as high as 100% but usually for ease of handling 50–80% by weight activities as preferred.

In the foregoing processes, the alkali metal sulfate may be sodium sulfate or potassium sulfate. The alkali metal hydroxide may be sodium hydroxide or potassium hydroxide and the alcohol may be methanol, ethanol or propanol. The ester of naphthenic may be methyl naphthenate, ethyl naphthenate or propyl naphthenate.

Naphthenohydroxamic acid is miscible at any ratio with aromatic and aliphatic hydrocarbon solvents. Useful hydrocarbon solvents include kerosene, petroleum ether, VMP naphtha, mineral spirits, Stoddard Solvent, diesel oil, benzene, toluene, xylene, other alkyl aromatic compounds, their mixtures and the like. Typical of the alkyl aromatic compounds used as solvents are those sold under the Panasol trademark by Amoco Chemical Corporation such as the RX and AN series. These solvents are liquid and essentially insoluble in water. They have specific gravities in the range from 0.5 to 0.9 and have a mid-boiling point in the approximate range of 120°F to 615°F (ASTM Distillation). In addition to these hydrocarbon solvents, chlorinated hydrocarbon solvents may also be used and in some instances may improve solubility. Accordingly, the term hydrocarbon solvents as used herein includes both the unsubstituted hydrocarbons and the chlorinated hydrocarbon solvents. The heavy syrupy naphthenohydroxamic acid is dissolved in one or more of the above hydrocarbon solvents to obtain an effective amount of chelating agent from about 0.01 to about 50% by weight of the acid in hydrocarbon solution when it is used in a hydrometallurgical process with the preferred being from about 1% to about 25% by weight of the acid.

Naphthenohydroxamic acid solutions prepared by the above methods are used as the chelator in hydrometallurgical processes to recover metal values. These processes are well-known and are described in the aforementioned U.S. Pat. No. 3,428,448.

The hydrometallurgical process disclosed herein may be used to recover metal values such as

| Metal Value | Symbol |
|---|---|
| Aluminum | Al |
| Bismuth | Bi |
| Cerium | Ce |
| Chromium | Cr |
| Cobalt | Co |
| Copper | Cu |
| Dysprosium | Dy |
| Erbium | Er |
| Europium | Eu |
| Gadolinium | Gd |
| Gold | Au |
| Holmium | Ho |
| Iridium | Ir |
| Iron | Fe |
| Lanthanum | La |
| Lead | Pb |
| Lutetium | Lu |
| Molybdenum | Mo |
| Nickel | Ni |
| Osmium | Os |
| Palladium | Pd |
| Platinum | Pt |
| Plutonium | Pu |
| Praseodymium | Pr |
| Radium | Ra |
| Rhodium | Rh |
| Ruthenium | Ru |
| Samarium | Sm |
| Terbium | Tb |
| Thallium | Tl |
| Thulium | Tm |
| Tin | Sn |
| Uranium | U |
| Vanadium | V |
| Ytterbium | Y |

-continued

| Metal Value | Symbol |
|---|---|
| Zinc | Zn |

These metal values are in the form of dilute solutions such as those obtained by the leaching operations described on pages 615–750 of Evans and Shoemaker, "International Symposium on Hydrometallurgy", (The American Institute of Mining, Metallurgical and Petroleum Engineers, Inc. N.Y., N.Y., 1973). Leaching can be effected by chemical and/or microbiological means and by using reagents such as acids, e.g., sulfuric acid or hydrochloride acid; bases, e.g., ammonium hydroxide or sodium hydroxide; salts, e.g., sodium sulfide or sodium cyanide; and gases dissolved in water, e.g., ammonia or sulfur dioxide. Leaching operations are well known in the art.

The use of a hydrocarbon solution of naphthenohydroxamic acid in a hydrometallurgical process may be illustrated by recovery of copper values from a dilute acid leach solution containing copper ions. In most commercial operations copper leach solutions have a pH in the range of from about 1.7 to about 3. Copper values are recovered from the aqueous leach solution by contacting the leach solution with a hydrocarbon solution containing naphthenohydroxamic acid. The copper ions and naphthenohydroxamic acid react to form a complex which is soluble in the hydrocarbon solvent. Reaction between the copper ions and naphthenohydroxamic acid is instantaneous so for all practical purposes only a few minutes contact time between the chelator and the copper ions is all the time that is required in most hydrometallurgical processes. Copper ions in dilute leach solutions containing up to 10 g/l can be extracted during a single pass or contact with the naphthenohydroxamic acid solution. With more concentrated copper solutions, it is preferable to use several passes to avoid phase separation difficulties such as emulsification of the hydrocarbon solution with the leach solution. In many processes, the pH of the copper leach solution is adjusted with ammonium to about 9.5 to about 11 before extraction.

After extraction of the aqueous leach solution with the naphthenohydroxamic acid in hydrocarbon solution, the hydrocarbon soluble copper complex of naphthenohydroxamic acid remains in the hydrocarbon phase. The hydrocarbon phase containing the copper complex is then separated from the leach solution and copper is stripped from the hydrocarbon solution by use of a dilute sulfuric acid solution, e.g., containing 2 to 5% by weight sulfuric acid. Use of a dilute sulfuric acid solution for stripping of the hydrocarbon phase not only permits frequent regeneration of naphthenohydroxamic acid but also avoids deterioration or decomposition of the naphthenohydroxamic acid by strong acid.

After the copper ions are stripped from the hydrocarbon phase, metallic copper is recovered from the acid solution by cementation on metallic iron or by electrowinning. Electrowinning is similar to electrolytic refining except that an insoluble anode is employed and the electrode arrangement is different. The electrowinning reactions are as follows:

The anode reaction is
$SO_4^{2-} + H_2O \rightarrow H_2SO_4 + \frac{1}{2} O_2 = 2e$ The cathode reaction is
$Cu^{2+} + 2e \rightarrow Cu$ The net reaction being $$CuSO_4 + H_2O \rightarrow Cu° + H_2SO_4 + \tfrac{1}{2} O_2$$

Further, hydrocarbon solutions of naphthenohydroxamic acid may be used to recover metal values from neutral or alkaline leach solutions as well as from ammoniacal solutions. These solutions may be used to recover specific metals such as copper and uranium as well as the rare earth metals and noble metals listed in the table above.

For a fuller understanding of the nature and objects of this invention, reference may be made to the following examples. These examples are given merely to illustrate the invention and are not to be construed in a limiting sense. All parts, proportions and quantities are by weight unless otherwise indicated. The terms, g, ml, l, °C, °F, min, in, ppm are used to indicate grams, milliliters, liters, degrees Centigrade, degrees Fahrenheit, minutes, inches, parts per million, respectively, in these examples.

EXAMPLE I

A. Preparation of methyl ester of naphthenic acid

A total of 600 g methanol and 300 g naphthenic acid were charged into a 2 liter reaction flask equipped with stirrer, thermometer and reflux condenser. The mixture was agitated until a clear solution was obtained. Then 20 g of 98% sulfuric acid was added to the solution. The solution was heated to reflux temperature (68°–69°C), refluxed for 5 hr, cooled to 20°C and the methanol was distilled off under vacuum. The maximum temperature during vacuum distillation was 40°C.

The mixture was transferred to a separatory funnel and allowed to stand undisturbed for 2 hr for phase separation. The bottom layer which was a 50% sulfuric acid in water solution was discarded and the upper layer which was methyl naphthenate was washed twice with a 5% sodium bicarbonate in water solution, dried with anhydrous sodium sulfate and filtered to obtain a total of 300 g methyl naphthenate. The ester had an acid value of 6 and a saponification value of 212.

B. Preparation of naphthenohydroxamic acid

To a 2 l reaction flask equipped with stirrer, thermometer and condenser and immersed in an ice-water-salt cooling solution was charged 64 g hydroxylammonium sulfate and 32 g water. The resulting slurry was stirred for 10 minutes and 48 g methanol added. The reaction mixture was then cooled to 0°C and 60 g of a 50% sodium hydroxide in water solution was added very slowly with good stirring at such a rate that the maximum temperature did not exceed 5°C. Sodium hydroxide addition required 1 hr and the final pH of the slurry was 7.8.

Then 90 g methanol and 160 g methyl naphthenate were added to the slurry and the cooling bath removed. A total of 132 g of a 25% potassium hydroxide solution in methanol was added very slowly over a 3 hr period with good agitation. The initial addition temperature was 25°C but rose gradually to 30°C. The mixture was stirred for 5 additional hr at 30°C, then 38 g acetic acid was added under cooling to adjust the pH to 7.5.

Methanol was removed by vacuum stripping, and then 320 g water was added to dissolve the solid sodium sulfate and potassium acetate. The mixture was then transferred to a separatory funnel and allowed to stand undisturbed for 2 hr for phase separation. The bottom salt-water layer was drawn off. The naphthenohydroxamic acid which was the upper layer was washed with a 10% sodium sulfate solution and transferred to a half liter flask. Then 50 g ethylene dichloride was added and the residual water removed from the product by azeotropical distillation under vacuum. After removal of all the water and solvent, the product was recovered as a heavy yellow colored syrup. Then 160 g kerosene was added to dissolve the syrup and to obtain 320 g of a 50% kerosene solution of the naphthenohydroxamic acid in the form of a mobile light yellow liquid.

EXAMPLE II

Samples of naphthenohydroxamic acid were prepared according to the procedures of U.S. Pat. 2,397,508, U.S. Pat. 2,818,429 and the procedure of this invention as described in Example I above. Maximum chelating capacity of each sample was determined by dissolving one gram (active basis) of each sample in 200 ml hexane and mixing this solution with a solution containing 10 grams of copper sulfate pentahydrate in 50 ml water for 3 hours. Each mixture was allowed to stand undisturbed and separated into two phases (layers). The upper layer containing the deep green solution of the copper complex was washed several times with a 10% by weight sodium sulfate solution, then the chelated copper was liberated from the copper complex in the hexane solution by extracting with 50% by weight sulfuric acid. The acid solution of copper was then diluted to one liter in a volumetric flask and the total copper content determined by atomic absorption and checked by a control method, the wet method using zinc dibenzyldithiocarbamate as the reagent.

The following results on the total chelating capacity of these three samples were obtained:

| Sample Prepared According To The Method In | % Copper Chelated |
|---|---|
| U.S. Pat. No. 2,397,508 | 7.8 |
| U.S. Pat. No. 2,818,429 | 15.8 |
| Example I of this Invention | 24.0 |

The methyl naphthenate ester used in the preparation of these three samples had a saponification value of 212 which corresponded to a molecular weight of 264. The theoretical maximum per cent of copper which could be chelated by any sample was 24.05. The above results show that the sample prepared by the method of this invention as described in Example I above chelated 24.0% and indicates that the method gave almost a 100% conversion of the ester to the hydroxamic acid compared to a 32.5% conversion by the method given in U.S. Pat. 2,397,508 and a 66% conversion by the method given in U.S. Pat. 2,818,429.

EXAMPLE III 11.789 g copper sulfate ($CuSO_4.5H_2O$) was dissolved in 900 g distilled water. 14.8 g of an aqueous ammonia solution was added to the copper sulfate solution. The mixture was transferred to a 1 liter volumetric flask and adjusted with distilled water to the 1 liter mark. Concentration of copper in the solution was 3 g/l (3000 ppm copper). The pH of the solution was 9.5. 200 ml of the copper solution containing 0.6 g copper and 200 ml of a kerosene solution containing 7 g of naphthenohydroxamic acid (3.5% active by volume) from Example I as the chelator were mixed together in an Erlenmeyer flask using a 2 in magnetic stirring bar. After 10 minutes of vigorous stirring, the mixture was transferred to a seperatory funnel and the phases separated. The aqueous bottom phase was analyzed for copper content (atomic absorption method) and showed a copper content of 0 ppm.

EXAMPLE IV

The organic phase from Example III which was the upper phase containing the solution of copper naphthenohydroxamic acid complex was mixed with 100 ml of a 2% sulfuric acid solution for 10 minutes in an Erlenmeyer flask using a 2 in magnetic stirring bar. The organic phase was mixed with the sulfuric acid solution to strip the copper from the organic phase and to regenerate the chelator in the organic phase. The organic phase containing the regenerated chelator was then separated from the sulfuric acid solution and used to extract a 3000 ppm copper solution following the procedure given in Example III. The regenerated chelator gave the same results as in Example III and the copper content of 200 ml of ammoniacal solution containing 3000 ppm of copper was reduced to 0 ppm.

EXAMPLE V 200 ml of an ammoniacal copper solution having a pH of 9.5 and containing 3000 ppm copper was mixed with 200 ml of a kerosene solution containing 3.5 g of naphthenohydroxamic acid (1.75% active by volume) from Example I as the chelator in an Erlenmeyer flask using a 2 in magnetic stirring bar. After stirring for 2 min, the mixture was transferred to a separatory funnel and the phases separated. The aqueous phase was analyzed for copper content. It was found that the copper content of the aqueous phase had been reduced to 800 ppm copper during the short contact time between the two phases even though the kerosene solution contained only one-half as much of the naphthenohydroxamic acid as was used in Example IV above.

EXAMPLE VI 108.065 g copper sulfate ($CuSO_4.5H_2O$), 19.7 g zinc chloride ($ZnCl_2$) and 2.184 g nickel acetate $Ni(C_2H_3O_2)_2.4H_2O$ were dissolved in 500 g distilled water. 300 g of an aqueous ammonia solution was added to the above solution. The mixture was transferred to a 1 liter volumetric flask and adjusted with distilled water to the 1 liter mark. Concentration of the metals in the solution was 27.5 g/l copper (27,500 ppm Cu), 9.45 g/l zinc (9,450 ppm Zn) and 0.515 g/l nickel (515 ppm Ni). The pH of the solution was 10.5. A 200 ml aliquot of the water solution was extracted four times with 400 ml portions of a 2.35% active by volume soltuion of naphthenohydroxamic acid from Example I dissolved in kerosene. The water solution was extracted using four passes. Contact time for each pass was 4 min. After each pass the phases were separated and analyzed for metal content. A fresh naphthenohydroxamic acid solution was used for each pass. Table I shows the ppm Extracted of each metal by each pass.

TABLE I

| | ppm Extracted | | |
|---|---|---|---|
| | Copper | Zinc | Nickel |
| Pass No. 1 | 7700 | 800 | 50 |
| Pass No. 2 | 7500 | 850 | 40 |
| Pass No. 3 | 7500 | 900 | 40 |
| Pass No. 4 | 3800 | 900 | 40 |

EXAMPLE VII

To effect a more efficient separation of copper from zinc, each of the organic phases obtained from the first three passes in Example VI was eluted using a 5% sulfuric acid solution. The resulting acid extractions were then combined. The ratio of copper to zinc in the three combined acid extractions was 8.9 parts copper to 1 part zinc. The pH of the acid solution was adjusted to 10.5 with aqueous ammonia and then extracted with a 2.35% active by volume solution of naphthenohydroxamic acid from Example I dissolved in kerosene solution. The organic phase was separated and analyzed for copper and zinc. It contained 40 parts copper to 1 part zinc as compared to the original water solution in Example V which contained 2.91 parts copper to 1.0 parts zinc. The copper-nickel ratio in the organic phase was 200 parts copper to 1 part nickel as compared to the original solution in Example VI which contained 53.4 parts copper to 1.0 part nickel.

EXAMPLE VIII 113.96 g copper sulfate ($CuSO_4.5H_2O$), 21.263 zinc chloride ($ZnCl_2$) and 2.226 g nickel acetate $Ni(C_2H_3O_2)_2.4H_2O$ were dissolved in 500 g distilled water. 320 g of an aqueous ammonia solution was added to the above solution and the total volume of the mixture was adjusted with distilled water to 1 liter. Concentration of the metals in the solution was 29 g/l copper (29,000 ppm Cu), 10.2 g/l zinc (10,200 ppm Zn) and 0.525 g/l nickel (525 ppm Ni). The pH of the solution was 10.5. A 200 ml aliquot of the water solution was extracted with four 200 ml portions of a 4.7% active by volume solution of naphthenohydroxamic acid from Example I dissolved in carbon tetrachloride. The water solution was extracted using 4 passes. Contact time for each pass was 4 min. After each pass, the phases were separated and analyzed for metal content. A fresh carbon tetrachloride solution of the chelator was used in each pass. Phase separation between the water solution and carbon tetrachloride solution was instantaneous. Table II shows the ppm Extracted of each metal by each pass.

TABLE II

| | ppm Extracted | | |
|---|---|---|---|
| | Copper | Zinc | Nickel |
| Pass No. 1 | 8000 | 600 | 50 |
| Pass No. 2 | 7500 | 700 | 50 |
| Pass No. 3 | 6500 | 800 | 50 |
| Pass No. 4 | 5500 | 900 | 50 |

EXAMPLE IX 147.362 g copper sulfate ($CuSO_4.5H_2O$) was dissolved in 500 g distilled water. 300 g of an aqueous ammonia solution was added to the copper sulfate solution. The total volume was adjusted with distilled water to 1 liter. Concentration of copper in the solution was 37,500 ppm (37.5 g/l). The pH of the solution was 10.5. 100 ml of the water solution was extracted with five 200 ml portions of a 2.35% active by volume solution of naphthenodroxamic acid from Example I dissolved in kerosene. The water solution was extracted using five passes. Contact time for each pass was 4 min and a fresh portion of the chelator solution was used for each pass. Table III shows the ppm Cu Extracted and the % Cu Extracted for each pass as well as the total ppm Cu Extracted and the total % Cu Extracted.

TABLE III

|  | ppm Cu Extracted | % Cu Extracted |
|---|---|---|
| Pass No. 1 | 8500 | 22.67 |
| Pass No. 2 | 8400 | 22.40 |
| Pass No. 3 | 8400 | 22.40 |
| Pass No. 4 | 8400 | 22.40 |
| Pass No. 5 | 3750 | 10.00 |
| TOTAL | 37450 | 99.87 |

EXAMPLE X

This example demonstrates use of a commercial benzophenone oxime chelator as described in aforementioned U.S. Pat. 3,428,449. This chelator is known commercially as LIX 64-N (General Mills) and is 50% active.

108.065 g copper sulfate ($CuSO_4.5H_2O$) was dissolved in 500 g distilled water. 225 g of an aqueous ammonia solution was added to the copper sulfate solution. The total volume was adjusted with distilled water to 1 liter. Concentration of copper in the solution was 27,500 ppm (27.5 g/l). The pH of the solution was 10.5. 100 ml of the water solution was extracted with five 200 ml portions of a kerosene solution containing 2.35% active by volume of this commercial benzophenone oxime chelator. The water solution was extracted using five passes. Contact time for each pass was 4 min. A fresh portion of the chelator solution was used for each pass. Table IV shows the ppm Cu Extracted and the % CU Extracted for each pass as well as the total ppm Cu Extracted and the total % Cu Extracted.

TABLE IV

|  | ppm Cu Extracted | % Cu Extracted |
|---|---|---|
| Pass No. 1 | 4700 | 17.09 |
| Pass No. 2 | 4500 | 16.36 |
| Pass No. 3 | 3800 | 13.82 |
| Pass No. 4 | 3700 | 13.45 |
| Pass No. 5 | 3600 | 13.09 |
| TOTAL | 20300 | 73.81 |

Comparision of the data in Table III and Table IV shows that the extraction rate is 32% to 66% greater with naphthenohydroxamic acid as the chelator. Further, Table III and Table IV show that in comparative tests using the same concentrations of chelating agent, a 37,500 ppm $Cu^{++}$ solution was reduced to 55 ppm $Cu^{++}$ with naphthenohydroxamic acid in five passes while the commercial chelator in five passes reduced a 27,500 ppm copper solution only to 7200 ppm $Cu^{++}$. At this rate, more than nine passes would be required to exhaust a 37,500 ppm $Cu^{++}$ solution with the commercial chelator to 50 ppm $Cu^{++}$. Otherwise, it would be necessary to use twice as much of the commercial chelating agent as naphthenohydroxamic acid.

EXAMPLE XI 100 ml of an aqueous solution containing 27,500 ppm copper and having a pH of 10.5 was extracted with five 200 ml portions of a kerosene solution containing 2.35% naphthenohydroxamic acid. The aqueous solution was extracted using five passes. Contact time for each pass was 4 min. and a fresh portion of the chelator solution was used for each pass. Table V shows the ppm Cu Extracted and the % Cu Extracted for each pass as well as the total ppm Cu Extracted and the total % Cu Extracted.

TABLE V

|  | ppm Cu Extracted | % Cu Extracted |
|---|---|---|
| Pass No. 1 | 7500 | 27.27 |
| Pass No. 2 | 7200 | 26.18 |
| Pass No. 3 | 6500 | 23.63 |
| Pass No. 4 | 5500 | 20.00 |
| Pass No. 5 | 750 | 2.73 |
| TOTAL | 27450 | 99.81 |

Comparison of the data in Table IV and Table V shows that the extraction rate with equal copper levels is about 60% greater with naphthenohydroxamic acid as the chelator. Further, Table IV and Table V show that more copper was extracted in 3 passes with the naphthenohydroxamic acid (77.08%) then with the commercial chelator in 5 passes (73.81%).

EXAMPLE XII

A 100 ml aliquot of a water solution containing 10 grams per liter uranium (10,000 ppm $UO_2^{++}$) was extracted with 100 ml of a kerosene solution containing 7.3 grams of naphthenohydroxamic acid. The extracted water solution was analyzed for residual uranium and found to have a uranium content of 55 ppm $UO_2^{++}$. Approximately 99.5% of the uranium was chelated and present in the kerosene phase. The kerosene phase was stripped with a 5% sulfuric acid solution and uranium was recovered from the acid extract by neutralization with ammonia. The regenerated naphthenohydroxamic acid in the kerosene phase showed no loss in chelating power for uranium.

EXAMPLE XIII

This example demonstrates the extraction of copper from an acid solution.

12.575 g copper sulfate ($CuSO_4.5H_2O$) was dissolved in 800 g distilled water. The volume of the solution was adjusted to 1 liter. The pH of the solution was 4.0. (The Cu content was 3200 ppm) 200 ml of the copper solution was extracted using five 200 ml portions of a kerosene solution of naphthenohydroxamic acid containing 7 g of the chelator. The copper solution was extracted using five passes. After each pass, the pH of the copper solution was readjusted with 50% sodium hydroxide solution to a pH of 4.0. Table VI shows the ppm Cu extracted in each pass as well as the total ppm Cu Extracted.

TABLE VI

|  | ppm Cu Extracted |
|---|---|
| Pass No. 1 | 850 |
| Pass No. 2 | 800 |
| Pass No. 3 | 800 |
| Pass No. 4 | 500 |
| Pass No. 5 | 250 |
| TOTAL | 3200 |

EXAMPLE XIV

This example demonstrates the extraction of uranium solutions with naphthenohydroxamic acid solutions. A total of 1.7818 g uranyl acetate ($UO_2(C_2H_3O_2)_2.2H_2O$) was dissolved in 950 g distilled water and the volume of the solution was adjusted to 1 liter. The solution contained 1000 ppm $UO_2^{++}$. The pH of the solution was 4.8. A 100 ml aliquot of the uranium solutuion was extracted with 100 ml of a kerosene solution containing 0.32 g of naphthenohydroxamic acid. The extracted water solution was analyzed for uranium content using a colorimetric determination method based on the reaction of dibenzoylmethane with uranium (VI). Uranium content of the solution was reduced from 1000 ppm $UO_2^{++}$ to 10.5 ppm $UO_2^{++}$. Approximately 99% of the uranium ions were chelated in the organic phase.

EXAMPLE XV

This example demonstrates extraction of a rare earth metal solution containing 1 g of lanthanum chloride ($LaCl_3$) dissolved in 100 cc distilled water. The solution contained 5460 ppm lanthanum and had a pH of 6.65. A total of 5 g of a 50% by weight naphthenohydroxamic acid in kerosene solution was diluted with 100 cc of kerosene.

The two solutions were mixed together and stirred on a magnetic stirrer plate for 15 min. The mixture was transferred to a separatory funnel for phase separation and the two phases separated. The lower water phase was analyzed for lanthanum according to the alizarin-sulfonate method in Sandell, Colorimetric Determination of Traces of Metals - Third Edition (Interscience Publisher, Inc., N.Y.,N.Y. 1959) and found to contain 109 ppm lanthanum.

The upper solvent phase was treated with 6 N nitric acid solution to elute lanthanum from the complex and the nitric acid water phase was analyzed for lanthanum content. Analysis showed 98% of the lanthanum value in the original $LaCl_3$ solution was recovered.

EXAMPLE XVI

This example demonstrates extraction of a noble metal solution prepared by dissolving 1 g of aurochloric acid ($HAuCl_4 \cdot 3H_2O$) containing 50.04% or 500.4 mg gold in 400 cc distilled water. The solution contained 1251 ppm Au and had a pH of 2.8. A total of 6 g of a 50% by weight naphthenohydroxamic acid in kerosene solution was diluted with 50 cc of kerosene. The two solutions were mixed together and stirred on a magnetic stirrer plate for 10 min. The mixture was transferred to a separatory funnel and the two phases separated.

The gold content of the water phase was analyzed according to the Rhodamine B Method in Sandell, Colorimetric Determination of Traces of Metals - Third Edition (Interscience Publishers, Inc., N.Y.,N.Y. 1959) and found to contain 0 ppm gold.

A sample of the solvent phase containing gold in form of a complex with naphthenohydroxamic acid was digested with a mixture of fuming nitric acid and sulfuric acid; the residue dissolved in a mixture of nitric and hydrochloric acids and analyzed for gold content. Analysis showed 100% of the gold in the original solution of aurochloric acid was recovered.

While the invention has been described with reference to certain specific embodiments thereof, it is understood that it is not to be so limited since alterations and changes may be made therein which are within full and intended scope of the appended claims.

What is claimed is:

1. In a process for producing naphthenohydroxamic acid from an ester of napthenic acid, the improvement comprising reacting at about 25°C to about 30°C about equimolar quantities of
   a. ester of naphthenic acid,
   b. hydroxylamine dissolved in an alcohol/water/alkali metal sulfate slurry wherein the water content of the slurry is insufficient to hydrolyze the ester during conversion to naphthenohydroxamic acid, and
   c. an alkali metal hydroxide dissolved in alcohol.

2. The process of claim 1 wherein the alkali metal sulfate is selected from the group consisting of sodium sulfate and potassium sulfate.

3. The process of claim 1 wherein the alcohol is selected from the group consisting of methanol, ethanol and propanol.

4. The process of claim 1 wherein the alkali metal hydroxide is selected from the group consisting of potassium hydroxide and sodium hydroxide.

5. The process of claim 1 wherein the slurry is prepared by:
   a. slurrying hydroxylammonium sulfate in water,
   b. adding alcohol to the slurry
   c. cooling the slurry to about 0°C to about 5°C,
   d. adding sufficient alkali metal hydroxide dissolved in water or alcohol to the slurry with agitation and cooling to a temperature below 5°C to adjust the final pH of the slurry to about 7 to about 8, and
   e. adding sufficient alcohol to adjust the weight ratio of alcohol to water in the slurry to from about 2:1 to about 3:1.

6. The process of claim 1 wherein naphthenohydroxamic acid is prepared by:
   a. slurrying hydroxylammonium sulfate in water,
   b. adding alcohol to the slurry,
   c. cooling the slurry to about 0°C to about 5°C,
   d. adding sufficient alkali metal hydroxide dissolved in water or alcohol to the slurry with agitation and cooling to a temperature below 5°C to adjust the final pH of the slurry to about 7 to about 8,
   e. adding sufficient alcohol to adjust the weight ratio of alcohol to water in the slurry to from about 2:1 to about 3:1, and
   f. reacting at about 25°C to about 35°C about equimolar quantities of the ester of naphthenic acid, the hydroxylamine slurry from (e) and alkali metal hydroxide dissolved in an alcohol.

7. The process of claim 1 wherein the hydroxylamine is dissolved in a methanol/water/sodium sulfate slurry.

8. The process of claim 1 wherein the hydroxylamine dissolved in alcohol-water-alkali sulfate slurry is prepared by:
   a. slurrying from about 64 to about 70 parts by weight of hydroxylammonium sulfate in from about 32 to about 40 parts by weight of water,
   b. adding from about 48 to about 60 parts by weight of alcohol,
   c. cooling at about 0°C to about 5°C,
   d. adding sufficient sodium hydroxide dissolved in water or alcohol with agitation and cooling at a temperature below 5°C to obtain a slurry having a final pH from about 7 to about 8, and
   e. adding sufficient alcohol to adjust the weight ratio of alcohol to water in the slurry to from about 2:1 to about 3:1.

9. The process of claim 1 wherein the ester of naphthenic acid is selected from the group consisting of methyl naphthenate, ethyl naphthenate and propyl naphthenate.

* * * * *

UNITED STATES PATENT AND TRADEMARK OFFICE
CERTIFICATE OF CORRECTION

PATENT NO. : 3,936,494
DATED : February 3, 1976
INVENTOR(S) : Stanley A. Lipowski It is certified that error appears in the above-identified patent and that said Letters Patent are hereby corrected as shown below:

Column 1, lines 56 and 57, "U.S. Pat. No. 3,428,488" should be --U.S. Pat. No. 3,428,449--. Column 5, line 38, "U.S. Pat. No. 3,428,448" should be --U.S. Pat. No. 3,428,449--.

Signed and Sealed this

Ninth Day of January 1979

[SEAL]

Attest:

RUTH C. MASON
Attesting Officer

DONALD W. BANNER
Commissioner of Patents and Trademarks